(12) United States Patent
Cheng et al.

(10) Patent No.: US 6,507,394 B1
(45) Date of Patent: Jan. 14, 2003

(54) METHOD AND APPARATUS FOR INSPECTING THE SURFACE OF A SEMICONDUCTOR DEVICE

(75) Inventors: Kun-Pi Cheng; I-Chung Chang, both of Hsin-Chu (TW)

(73) Assignee: Taiwan Semiconductor Manufacturing Co., Ltd, hsin Chu (TW)

(*) Notice: Subject to any disclaimer, the term of this patent is extended or adjusted under 35 U.S.C. 154(b) by 0 days.

(21) Appl. No.: 09/449,884

(22) Filed: Nov. 30, 1999

(51) Int. Cl.⁷ ................................................. G01N 21/00
(52) U.S. Cl. ................................. 356/237.5; 356/237.4
(58) Field of Search ........................ 356/237.1, 237.2, 356/237.3, 237.4, 237.5, 445, 448, 376, 378; 250/559.4, 559.41, 559.42, 559.44, 559.45, 559.46, 559.48

(56) References Cited

U.S. PATENT DOCUMENTS

| | | | | |
|---|---|---|---|---|
| 4,818,879 A | * | 4/1989 | Kajikawa | 250/548 |
| 4,933,567 A | * | 6/1990 | Silva et al. | 250/572 |
| 5,463,459 A | * | 10/1995 | Morioka et al. | 356/237 |
| 5,495,337 A | * | 2/1996 | Goshorn et al. | 356/376 |
| 5,818,061 A | * | 10/1998 | Stern et al. | 250/559.29 |
| 5,898,181 A | * | 4/1999 | Vurens | 250/559.28 |
| 5,926,266 A | * | 7/1999 | Dorundo et al. | 356/237.2 |
| 6,052,191 A | * | 4/2000 | Brayden, Jr. et al. | 356/381 |

* cited by examiner

*Primary Examiner*—Michael P. Stafira
(74) *Attorney, Agent, or Firm*—Tung & Associates

(57) ABSTRACT

An optical inspection system for detecting defects on the surface of a semiconductor wafer includes two light sources and two light receivers mounted as a common assembly which is rotated such that two curtains of light and corresponding linear photosensor arrays circularly scan the wafer surface. The reflected light is analyzed to determine the presence of surface defects. Marks applied to the wafer surface provide amplitude and timing references used to adjust and synchronize the analyzed signals.

7 Claims, 2 Drawing Sheets

METHOD AND APPARATUS FOR INSPECTING THE SURFACE OF A SEMICONDUCTOR DEVICE

TECHNICAL FIELD

The present invention broadly relates to non-contact inspections systems and methods, and deals more particularly with a method and apparatus for inspecting the surface of semiconductor device such as a semiconductor wafer.

BACKGROUND OF THE INVENTION

In connection with processes used to fabricate semiconductor devices, such as semiconductor wafers, uniformity and consistency from device-to-device, and from batch-to-batch are critical in achieving high yield and superior device quality. A series of successive processes are carried out in order to complete fabrication of a semiconductor wafer. These processes rely on carefully controlled processing parameters, as well as controlled processing environments in order to achieve high quality wafers. Nevertheless, some variations do occur during the fabrication process that can result in one or more localized defects in the surface of the wafer. When the wafer is sliced into individual die, those die within the localized defect are must be discarded, thus resulting in scrap and reduced yield. It is therefore critical in such fabrication processes to identify, through some means of inspection, those localized areas on the wafer which contain defects. Such defects may be as the result of too little or too great of material coating thickness within certain areas on the wafer, or as the result contaminants having been deposited on the wafer surface.

In the past, wafer surface quality, uniformity and defects were assessed using purely visual means, wherein an operator would place the wafer under a microscope and view the wafer surface under magnification to identify localized defect areas. This manual process was not only time consuming and tedious, but was not always entirely effective in identifying defects. Although non-contact inspections systems have long been used in semiconductor manufacturing processes to aid in determining the position and placement of components or certain features on a device surface, such inspection methods are not suitable for use in identifying surface defects on a semiconductor wafer.

Accordingly, there is a clear need in the art for an improved inspection method and apparatus which overcome each of the shortcoming of the prior art discussed above.

BRIEF DESCRIPTION OF THE INVENTION

According to one aspect of the invention, a method is provided for inspecting the surface of a semiconductor device, such as a semiconductor wafer, which comprises the steps of: directing a beam of light through an optical element onto the surface of a semiconductor device; receiving light reflected from a surface which originates from the optical element; measuring a characteristic of the received light; and, scanning the surface of the device while relatively moving the device and the optical element.

The light is preferably formed in a curtain defining a line of light impinging on the device surface, and the relative movement is preferably produced by rotating the line of light about an axis essentially perpendicular tot he surface of the device. The reflected light is preferably passed through an optical receiver or detector which is rotated relative to the semiconductor device, in synchronization with a light beam, also about an axis perpendicular tot he surface of the device. In order to aid in precisely locating the surface defects, reference marks are applied to the device surface which are detected during the scanning process and provide a frame of reference for locating defects.

According to another aspect of the invention, a method for inspecting the surface of a semiconductor device is provided, which comprises the steps of: rotating a curtain of light impinging on the surface of the wafer such that the wafer surface is scanned by the light; rotating an optical receiver in synchronization with the rotation of the light curtain; receiving light in a receiver which is reflected from the surface of the wafer; and, analyzing the light received by the optical receiver.

The analysis is preferably performed by measuring the amplitude of the received light as a function of a rotational position of the optical receiver.

According to still another aspect of the invention, apparatus is provided for inspecting the surface of a semiconductor wafer which comprises; light source means for directing a line of light onto the surface of the wafer; an optical light receiver for receiving light reflected from the surface and originating from the light source; means for rotating the light and the receiver about an axis essentially perpendicular to the wafer; and, means for analyzing the light received by the receiver. The optical receiver preferably includes a linear photosensor array. Means are provides for locatably mounting the light source and a receiver, and motor means are provided for rotating the mounting means.

According to still another aspect of the invention, apparatus is provided for inspecting the surface of a semiconductor wafer comprising: first and second light sources for respectively directing first and second lines of light on to the surface of the wafer; first and second optical receiver for respectively receiving light reflected from the wafer surface and originating from the light sources; mans for analyzing the light received by the optical receiver; means for mounting the light sources and receivers as a single, common assembly; and, means for rotating the assembly about an axis extending essentially perpendicular to the wafer surface.

Accordingly, it is the primary object of the present invention to provide a method and apparatus for inspecting the surface of a semiconductor wafer.

A further object of the invention is to provide a method and apparatus as described above which provides highly reliable inspection results which are superior to that attainable by manual, visual inspection.

A still further object of the present invention is to provide a method and apparatus as aforementioned, in which the inspection process is performed quickly and automatically.

Another object of the present invention is to provide a method and apparatus as described above which allows complete automation of the inspection process so as to be suitable for inspecting a plurality of semiconductor wafers in rapid succession.

Another object of the present invention is to provide a method and apparatus of the type mentioned above which allows locating, with high precision, and recording the location of surface defects.

These, and further objects and advantages of the invention will be made clear or will become apparent during the course of the following description of the preferred embodiment of the present invention.

BRIEF DESCRIPTION OF THE DRAWINGS

In the drawings In the drawings, which form an integral part of the specification and are to be read in conjunction therewith, along with the appended claims, and wherein like reference numerals are employed to designate identical components in the various views:

DETAILED DESCRIPTION OF THE PREFERRED EMBODIMENT

Figure 1:
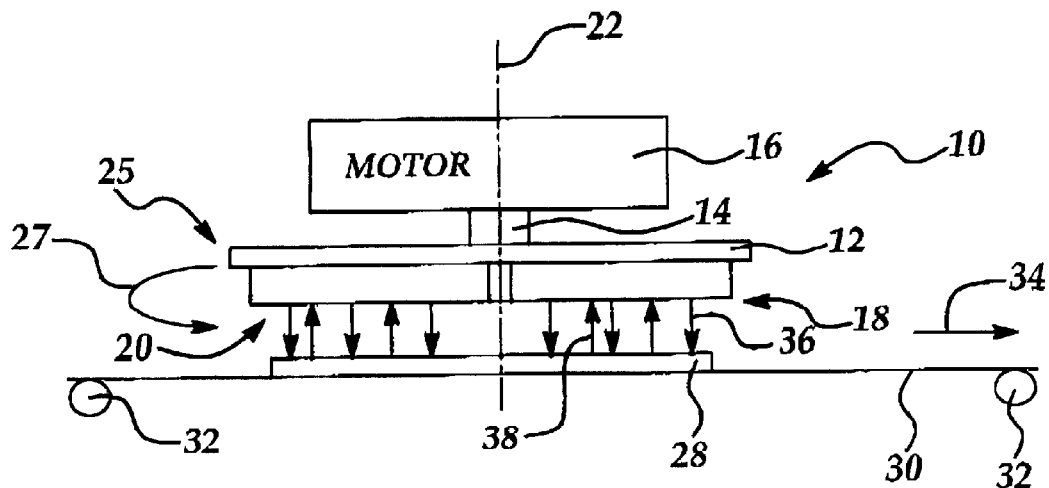
FIG. 1 is a diagrammatic, side view of apparatus for inspecting the surface of a semiconductor device, which forms the preferred embodiment the present invention and is useful in carrying out the related inventive method.

Referring now to the drawings, the present invention broadly involves a method and apparatus for identifying and automatically recording localized defects present on the surface of a semiconductor device, such as the semiconductor wafer 28. The various processes employed for producing semiconductor wafers 28 are well known inn the art, and need not be repeated herein. Such processes are tightly controlled, but nevertheless localized defects may be created in the surface of the wafer 28, for a variety of reasons. In some cases, defects are related to too great or too little of a coating thickness. In other cases, foreign particles may be introduced onto the wafer surface which render the localized defect area useless for yielding an acceptable semiconductor die.

In accordance with the preferred embodiment of the present invention, a non-contact method and apparatus 10 is provided for automatically scanning the surface of the wafer 28, in a completely automatic manner, in order to identify and precisely locate each surface defect.

The apparatus 10 includes an inspection head generally indicate by the numeral 25 which is secured to an output shaft 14 of a motor 16 which rotates the head 25 about an axis 22 extending essentially perpendicular to the surface of the wafer 28. In order to automate the inspection process so that a plurality of the wafers 28 may be inspected in relatively rapid succession, the wafers 28 may be placed on a conveyor 30 driven by rollers 32 which move the wafers 28 linearly beneath the rotating head 25, in the direction of the arrow 34. The rate of linear travel of the wafer 28 in the direction 34 is coordinated in timing with the rotational speed of the head 25 which may be rotated in either rotational direction, but herein is shown as being rotated in a counterclockwise direction, indicated by the arrows 27. The motor 16 can be of a direct drive DC type, however, any other suitable motive means may be employed for rotating inspection head 25 at the desired speed. Alternatively, of course, the wafer 28 could be rotated while the head 25 remains stationary, but this latter arrangement is potentially more complex in terms of the necessary equipment, especially if it is desired to process a plurality of wafers 28 in rapid succession.

The inspection head 25 includes two inspection head portions 18 and 20 secured on the bottom face of a mounting plate or bracket 12 so as to rotate with the latter as a common assembly. Each of the head portions 18, 20 includes an elongated optical light source 26, and an elongated optical receiver or detector 24 arranged in side by side relationship. The two head portions 18, 20 are arranged in end to end relationship to each other, along a common axis so as to be 180 degrees out of phase with each other as they rotate about axis 22. The light source 26 may comprise any suitable source of collimated light such as a laser, or conventional collimated light source which directs light through an optical element which that a curtain of light which is directed onto the surface of a wafer 28 at a pre-selected angle and impinges such surface along a line that extends radially outward from the central axis 22 so as to sweep or scan the entire wafer surface as the head 25 is rotated. The optical receiver 24 may comprise any of several conventional light detectors, such as a commercially available linear photosensor array or linear CCD. The receiver is arranged such that it normally receives a majority of light output from the source 26 which is reflected on the wafer surface at a known angle. It may be appreciated that each of the inspection head portions 18, 20 direct a curtain of light down onto the wafer surface and detect the reflection of this light. In FIG. 1, the light energy directed downwardly from the head 25 is indicated by the numerals 36, while the light energy reflected from the wafer surface is indicated by the numeral 38.

Figure 2:
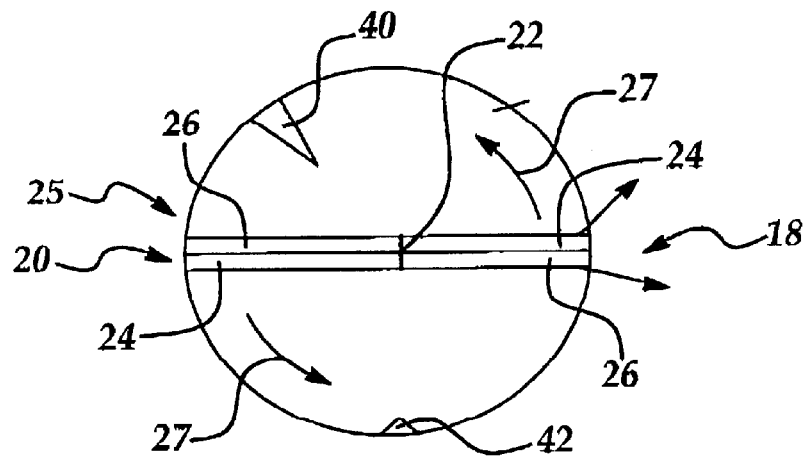
FIG. 2 is a diagrammatic, plan view showing a semiconductor wafer with the inspection head and forming part of the apparatus shown in FIG. 1, depicted in superimposed relationship to the wafer.
Figure 3:
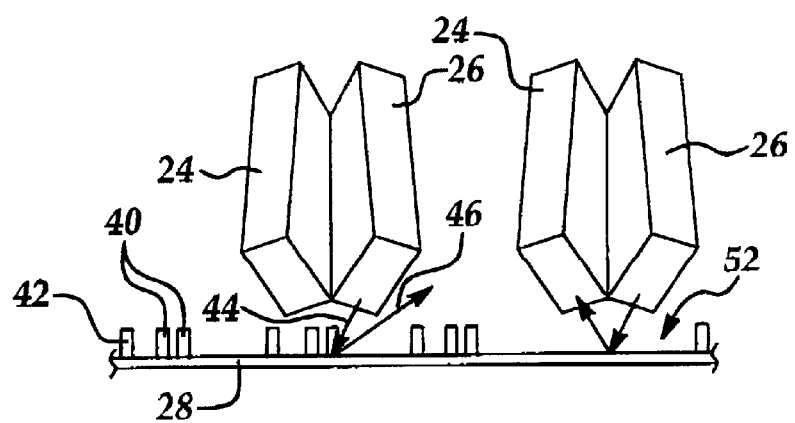
FIG. 3 is a diagrammatic view showing the components of the inspection head relative to the wafer surface which has a localized area of poor coating.
Figure 4:
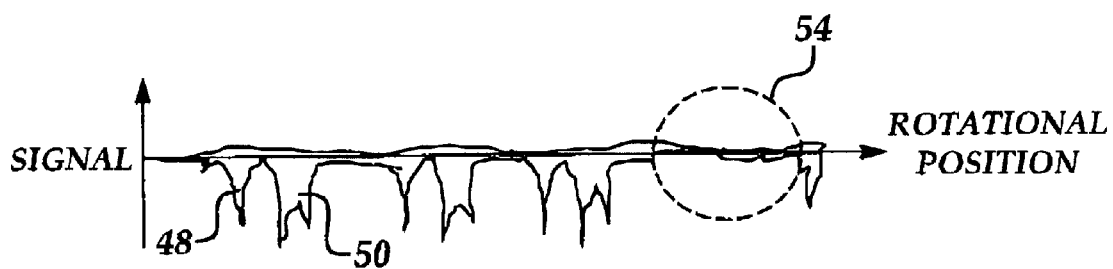
FIG. 4 is a plot of the amplitude of the received light reflected from the surface of a wafer shown in FIG. 3, as the function of the rotational position of the wafer.
Figure 5:
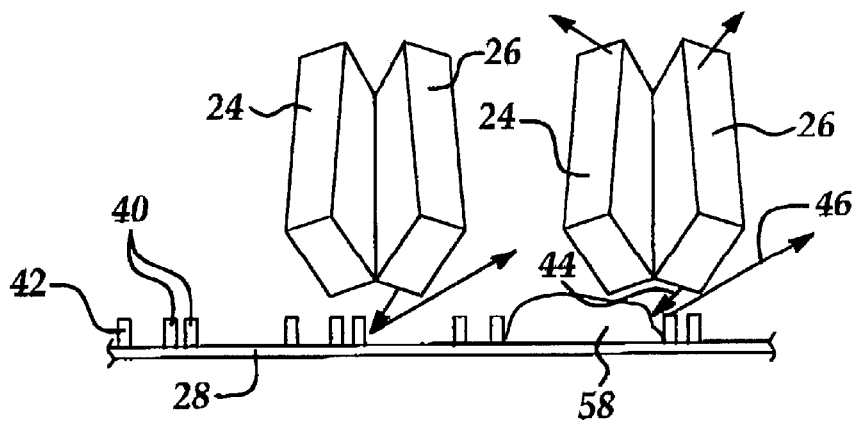
FIG. 5 is a view similar to FIG. 3 but depicting the presence of a foreign particle on the surface of a wafer.

In order to determine the precise rotational position of the inspection head 25 relative to a particular wafer 28, one or more reference marks may be placed on the surface of the wafer 28, two of such marks being shown in FIG. 2 and designated by the numerals 40, 42. The reference marks 40,42 may be placed on the wafer surface temporarily, or may be integrally formed as an integral part of the wafer surface. In any event, the reference marks 40, 42 allow the inspection system to record the precise location of any surface defects that are detected. As the head 25 is rotated, the reference marks 40, 42 result in an alteration of the reflected light detected by the receiver 24. In the case where the analyzer 24 analyzes the amplitude of the reflected light, reference marks 40, 42 produce markers 48, 50 appearing as amplitude peaks of known magnitude, repeatedly occurring in known timing relative to each other. As shown in FIG. 3, when the timing marks 40, 42 are beneath one of the optical head portions 18, 20 light rays 44 impinging the surface of the wafer 28 are reflected by the marks 40, 42 at an angle away from the receiver 24, thus changing the amplitude or intensity of the light that is detected and recorded. Essentially, inspection head 25 scans the surface of the wafer 28 to detect variations in the wafer surface. Detected variations in intensity can be characterized and correlated to particular types of surface defects. For example, as shown in FIG. 3, if a particular localized are of the wafer surface has an inordinately thin coating of material applied thereto, this coating thickness variation will be detected as a change in intensity or amplitude of a reflected light. This defective condition of insufficient coating thickness is designated on a plot of FIG. 4 by the reference numeral 54.

Figure 6:
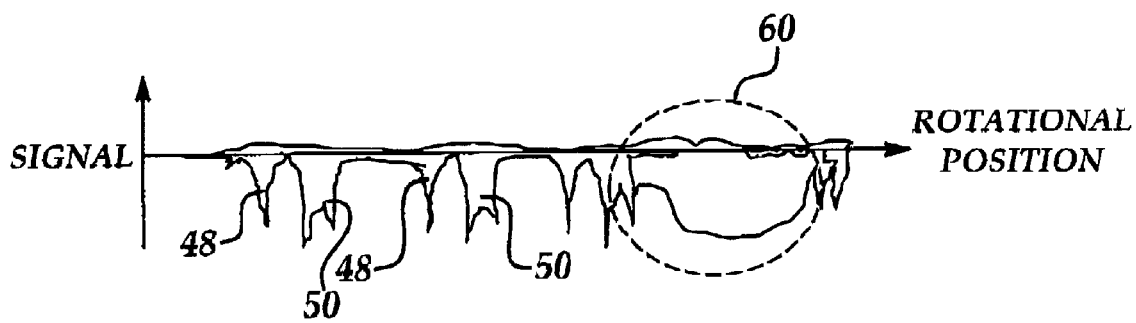
FIG. 6 is a view similar to FIG. 4 but showing the effect of the presence of the foreign particle shown in FIG. 5.

In the case where the contaminated particle 58 is present on the surface of the wafer 28, a change in the detected light intensity will also occur, which results in the recordation of a corresponding signal amplitude variation, designated by the numeral 60 in FIG. 6.

According to the foregoing description of the apparatus and its operation, it may be appreciated that the present invention provides a novel method for inspecting the surface of a semiconductor wafer, comprising the steps of: rotating a column of light impinging on the surface of the wafer such that the wafer surface is scanned by the light; rotating an optical receiver in synchronization with the rotation of the light curtain; receiving light in a receiver which is reflected from a surface of the wafer; and, analyzing the light received by the optical receiver.

From the foregoing, it is apparent that the method and apparatus described above not only provides for the reliable accomplishment of the objects of the invention, but do so in a particularly effective and economical manner. It is recognized, of course, that those skilled in the art may make various modifications or additions chosen to illustrate the invention without departing from the spirit and scope and contribution of the present invention. Accordingly, it is to be understood that the protection sought and to be afforded hereby shall be deemed to extend to the subject matter claimed and all equivalents thereof fairly within the scope of the invention.

What is claimed is:

1. A method of inspecting the surface of a semiconductor device, comprising the steps of:
  (A) directing light through an optical element forming a curtain of light that impinges on the surface of said device;
  (B) receiving light reflected from said surface and originating from said curtain of light by passing said reflected light through an optical receiver;
  (C) measuring a characteristic of the light received in step (A); and
  (D) scanning the surface of said device by rotating said curtain of light about an axis essentially perpendicular to the surface of the device and by rotating said optical receiver about said axis in synchronization with the rotation of said curtain.

2. The method of claim 1, wherein step (C) is performed by measuring the quantity of said reflected light.

3. The method of claim 1, wherein step (D) is performed by rotating a pair of optical sensors about an axis essentially perpendicular to said device surface.

4. The method of claim 1, including the steps of:
  applying at least one reference mark on said device;
  detecting said mark during step (D);
  (E) analyzing the mark detected in step (D); and
  (F) controlling step (D) based on the result of the analysis performed in step (E).

5. The method of claim 1, wherein step (D) includes measuring the amplitude of said light as a function of the rotational position of said optical receiver.

6. The method of claim 1 including the step of moving said semiconductor device linearly instead of rotationally relative to said light curtain and said optical receiver.

7. The method of claim 1, including the step of applying at least one reference mark on the surface of said semiconductor device, and step (D) includes sensing the presence of said mark as a function of said light curtain and said optical sensor.

* * * * *